United States Patent [19]

Rohowetz et al.

[11] 4,155,895

[45] May 22, 1979

[54] THERMOTROPIC INK

[75] Inventors: Stanley E. Rohowetz, Barrington, Ill.; James D. Specht, Neenah; Lee J. Murray, Appleton, both of Wis.

[73] Assignee: American Can Company, Greenwich, Conn.

[21] Appl. No.: 910,790

[22] Filed: May 30, 1978

[51] Int. Cl.$^2$ ............................ C08R 5/05; C08R 5/13
[52] U.S. Cl. .............................. 260/33.4 R; 106/14.5; 106/21; 106/22; 252/408; 422/57
[58] Field of Search .................. 260/33.4 R; 106/14.5, 106/21, 22; 23/253 TP; 252/408 R

[56] References Cited

U.S. PATENT DOCUMENTS

| | | | |
|---|---|---|---|
| 1,271,393 | 7/1918 | Voorhocet | 260/33.4 R |
| 2,606,654 | 8/1952 | Davis et al. | 106/21 UX |
| 4,015,937 | 4/1977 | Miyamoto et al. | 23/253 TP |
| 4,021,252 | 5/1977 | Banczak et al. | 106/26 |
| 4,024,096 | 5/1977 | Wachtel | 106/22 |
| 4,042,545 | 8/1977 | DeFago et al. | 106/21 |
| 4,045,397 | 8/1977 | Parkinson | 260/33.4 R |

Primary Examiner—William E. Schulz
Attorney, Agent, or Firm—Robert P. Auber; Ira S. Dorman; Ernestine C. Bartlett

[57] ABSTRACT

An ink composition is provided which is suitable for use on bare metal, for example, tinplate or aluminum as well as on such metals having organic coatings applied to surfaces thereof. The compositions may also be used on plastic containers or retortable pouches comprising plastic or plastic-metal foil laminates. The inks are suitable for use in contact printers or in jet ink printing techniques. The ink compositions are thermotropic, i.e. they change color in the presence of steam at elevated temperature and are useful as sterilization indicators. The inks comprise essentially a binder resin component, an alcohol solvent and a colorant which reacts in the presence of steam at elevated temperature to produce a visible and permanent color change.

26 Claims, No Drawings

THERMOTROPIC INK

BACKGROUND OF THE INVENTION

List of Prior Art

The prior art appears to be best exemplified by the following patents which were developed in a search:

| | | |
|---|---|---|
| Hainsworth | 2,798,855 | July 9, 1957 |
| Hainsworth | 2,798,856 | July 9, 1957 |
| Crone | 3,078,182 | Feb. 19, 1963 |
| Carumpalos | 3,288,718 | Nov. 29, 1966 |
| Edenbaum | 3,360,337 | Dec. 26, 1967 |
| Bhiwandker | 3,523,011 | Aug. 4, 1970 |
| Silva | 3,667,916 | June 6, 1972 |
| Emigh | 3,684,737 | Aug. 15, 1972 |
| Verses | 3,704,096 | Nov. 28, 1972 |
| Chapman | 3,862,824 | Jan. 28, 1975 |
| Banczak | 4,021,252 | May 3, 1977 |
| Wachtel | 4,024,096 | May 17, 1977 |
| Parkinson | 4,045,397 | Aug. 30, 1977 |
| Hwang | 4,070,322 | Jan. 24, 1978 |

FIELD OF THE INVENTION

The invention of this application relates to ink jet printing compositions and their use as color change indicators. The compositions are particularly useful as sterilization and/or moist thermal exposure indicators.

Ink jet printing techniques, although of comparatively recent development in the art of applying decorative and/or identifying indicia to a substrate, are of increasing importance. In general, such techniques impose rigid requirements on the ink compositions. To be suitable for use as a jet ink, the compositions must meet rigid requirements of viscosity and resistivity, solubility, compatibility of components and wettability of substrate; the ink must be quick-drying and smear resistant without clogging the ink jet nozzle and must permit rapid clean-up of the machine components with minimum effort. At the same time, such compositions must also be adapted for satisfactory performance in the particular end use for which they are specifically intended. For example, where the ink is to be employed in the printing of metal substrates, for example, coated and uncoated tinplate or aluminum, the ink must properly wet the bare metal surface and, where the surface is coated, it is highly desirable that some penetration of the coating be effected. In addition to proper wetting and/or penetration of the surface to be printed, the ink must also adhere strongly and be resistant to abrasion or moisture. It has been particularly difficult to obtain satisfactory adhesion and to maintain such adhesion to metal surfaces which are subjected to sterilization processes involving the combination of moisture and high temperature.

Apart from the jet ink applications of the ink, another area of interest in the art is the provision of printable sterilization indicators. Such compositions have heretofore usually utilized pigment combinations and have been applied primarily in determining whether proper sterilization heat has been applied to objects used in medical and surgical procedures. In the food packaging industry, for example, where metal cans are printed, filled with product, sealed and the package subjected to conditions of high temperature and moisture during pasteurization or sterilization techniques, there is a need for such compositions that are printable by either contact or jet ink techniques, that exhibit sufficient adhesion to the substrate to withstand the moisture and high temperature conditions of sterilization and which, at the same time, undergo a visible and permanent color change.

The provision of such an ink composition which shows a distinct difference in color among unsterilized and completely sterilized package provides for ready visible inspection and permits tracing a particular package or package after they have been processed. The invention thus provides a positive and visible indication that temperatures were reached at which sterilization or pasteurization of the products may be achieved.

It is an object of this invention to provide ink compositions, suitable for use in ink jet printing techniques, that exhibit excellent adhesion when exposed to moisture and elevated temperature conditions and which undergo a visible color change when so exposed.

It is another object of this invention to provide ink compositions, suitable for use in contact printing techniques, that exhibit excellent adhesion when exposed to moisture and elevated temperature conditions and which undergo a visible color change when so exposed.

Yet another object of this invention is to provide ink compositions capable of exhibiting excellent adhesion to coated and uncoated metal substrates and plastics and undergoing a visible color change when exposed to moisture and high temperature.

These and other objects of the invention will be apparent from the description of the invention which follows.

SUMMARY OF THE INVENTION

This invention relates to a thermotropic ink composition particularly adapted for use as a jet ink composition which comprises a resin binder, a thermotropic dye, a solvent blend and a surfactant. More specifically, the compositions comprise a solution compatible resin of the phenol-formaldehyde or resorcinol-formaldehyde class, a thermochromic dye that reacts at elevated temperature in the presence of steam to undergo a visible color change, a solvent blend consisting essentially of a lower alcohol or mixture thereof with methyl or ethyl cellosolve, dimethyl formamide or dimethyl sulfoxide, a surfactant and, optionally, an electrolyte.

DETAILED DESCRIPTION OF THE INVENTION

As described hereinabove, the ink compositions of this invention contain a reactive thermochromic dye, a solvent blend, a resinous binder component, a surfactant and other optional components, each of which must be in carefully balanced proportion to achieve successful operation of the ink in a jet printing apparatus and suitable properties as color-change indicators for use on coated and uncoated metal and plastic surfaces.

In general, the inks of this invention exhibit the following characteristics for use in ink jet printing systems: (1) a viscosity of about 1–5 cps at ambient temperatures; (2) surface tensions for use on metal surfaces of between about 20 and 27 dyne cm. (3) specific resistivity within the range of about 700 ohm cms. to about 1500 ohm cms.

The inks upon application should be water resistant within 30 seconds and dry to the touch within 60 seconds and exhibit a visible color change when exposed to temperatures of at least about 215° to about 230° F. and higher.

The Resin Binder

The resins preferred for use herein are best classified as phenolic heat-sensitive resins of the resole type. Such resins include those derived from phenol-formaldehyde, resorcinol-formaldehyde, etc. Suitable resole resins for use herein are solution compatible, alcohol soluble cross-linked polymers or prepolymers having molecular weights within the range of about 1,300 to about 10,000. Such resins are alkaline catalyzed phenol-formaldehyde condensation products in which the ratio of formaldehyde to phenol is greater than one and are usually identified as "B-stage" resins which are curable at elevated temperature by further condensation and/or cross-linking through hydroxymethyl groups to insoluble, chemically resistant, adherent polymers. Such resins are well known in the art. A preferred resin for use herein is commercially available under the trade name BLS-2700 or BKS 2600 from Union Carbide Corp. Such alcohol-soluble binders may be employed as such or they may be modified by admixture with other resins including polyvinyl butyral, polyvinyl acetate, polyacrylics, ethylene-acrylic copolymers, polyamides, or other phenolics etc. In general, the binder will be present in the composition in amounts ranging from about 3 to about 30% by weight and preferably from about 5% to about 10% by weight of the ink composition.

The use of resole phenolic resins, described hereinabove, is believed to be critical to the successful operation of the inks as color-change indicators. It is believed to be essential to the intended result that the resins be such that are susceptible to further curing after application to the substrate under the same conditions by which the dye component reacts to undergo a color change. Resole phenolic resins as described herein are soluble in the ink solvent, solution compatible with the components of the ink composition and when applied to the substrate undergoes further condensation upon subjection to high temperature, i.e. above about 215° F. to produce an adherent, insoluble binder for the ink components. A primary effect of the resin is to prevent undue dye leaching during the steam or moist thermal processing. While the mechanism by which the resin-dye combination functions to convey the desired characteristics to the ink composition is not fully understood, it is believed that the resin cures under the reaction condition with an accompanying release of water which in turn possibly serves to accelerate the thermotropic color change of the dye.

If desired, various acidic compounds may be incorporated in the resin component in catalytic amounts to accelerate the resin cure and/or color transition of the composition. Suitable compounds for this purpose include inorganic acids, for example phosphoric acid; esters of such acids, for example dibutyl amino pyrophosphate; organic acids, for example p-toluene sulfonic acid, oxalic acid, etc; metal salts, for example stannous chloride, ferric chloride, etc.

The Thermotropic Dye

Suitable dyes for use in this invention are those which undergo a visible and permanent color change when exposed to temperatures above about 215° F. in the presence of moisture. In addition to such thermotropic characteristics, the dye must also be soluble in the ink solvents and compatible with components thereof.

A preferred class of dyes are those which may be classified as substituted phenazines and diazotization products thereof derived by diazotization of safranines, e.g. 3,7-diamino-2,8-dimethyl-5-phenyl-phenazinium chloride with naphthols, phenols, aminobenzenes, etc. Representative dyes may be represented by the formula:

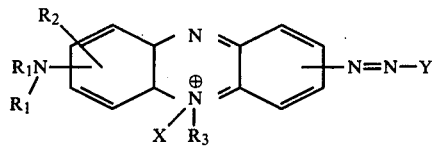

wherein $R_1$ and $R_2$ are lower alkyl radicals or hydrogen, X in an anion, for example, $Cl^-$, $Br^-$,; $R_3$ is an aromatic hydrocarbon radical, for example phenyl, tolyl, xylyl, etc. and Y is an aromatic hydrocarbon radical or substituted aromatic hydrocarbon radical, for example, B-hydroxy-naphthyl, p-dimethyl aminophenyl; p-hydroxyl-phenyl; 2hydroxyl-4-ethyl amino-5- methyl-phenyl; 1,2-dihydroxypropyl-4-amino-phenyl, etc.

Exemplary of such dyes are those available commercially as Janus Green B (C.I. Blue 11050); Janus Blue or Indoine Blue (C.I. 12211); Janus Black (C.I. 11825); Copying Black SK (C.I. 11957) and Copying Black 1059/1527 (C.I. 11090).

Although the mechanism by which the dyes of the invention undergo a color change are not known with certainty, it is believed that the thermotropic dye undergoes a chemical reduction of the azo linkage under the conditions of the sterilization or pasteurization resulting in a residual color forming moiety similar to that of Safranine O(3,7-diamino-2,8-dimethyl-5-phenyl-phenazinium chloride).

It is contemplated that other dyes not specifically enumerated, but of sufficient compatibility and solubility and reactive under the described conditions to undergo a color change, may also be employed.

In general, the dyes are present in the composition in amounts varying from about 0.1% to about 5% by weight of the composition.

The preferred dyes are the azo-phenazine class of dyes enumerated above which have been found to exhibit a dark blue color upon application to the substrate and to undergo a color change ranging from pink to red after being subjected to a temperature of at least about 215° F. in the presence of steam for periods ranging from about 2 to 90 minutes. In general, a readily visible color change will be evidenced in as little as 5 minutes depending on the particular temperature.

The Solvent Blend

Although minor amounts of other solvents may be included in the overall ink composition, the primary solvent is one or more of the lower aliphatic alcohols having 1 to 3 carbon atoms, either individually or in blends thereof. Methanol, ethanol and mixtures thereof are preferred. Additional solvents in which the dye has a high solubility or which aid in penetrating organic coatings on the substrate may also be included. Certain of the relatively low molecular weight glycol ethers such as ethylene glycol monomethyl ether (methyl cellosolve), and ethylene glycol monoethyl ether (ethyl cellosolve) as well as other more polar solvents such as dimethyl-formamide or dimethyl sulfoxide may also be included. The solvent blend will generally comprise from about 65 to about 97% of the ink composition. The solvent itself may vary from 100% lower alcohol to as little as about 25% alcohol with the remainder of the blend being the auxiliary solvents methyl cellosolve, dimethyl formamide, etc.

Surfactants and electrolytes are optional components that may be added to the compositions of the invention, if desired. Suitable examples are nonionic surfactants including fluorinated alkyl esters (commercially available under the trade name of FC-430, FC-431 and FC-170 from Minnesota, Mining and Manufacturing Co.). Lithium chloride, dimethyl amine hydrochloride, etc. are examples of suitable electrolytes. FC-430 is the preferred surfactant which may be present in amounts of about 0.01% to about 0.1% by weight. The preferred electrolyte is dimethyl amine hydrochloride which may be present in amounts from about 0% up to about 2% by weight of the composition.

The following examples are illustrative of ink compositions according to this invention which are effective thermotropic jet inks.

EXAMPLE 1

The following composition was formulated:
5% BLS-2700 (phenolformaldehyde resole resin)
1% Indoine Blue
47% Methanol
47% Methyl Cellosolve
0.01% FC-430 surfactant The resulting ink had a viscosity of 1.8 cps, a resistivity of 1800 ohm/cm., and a surface tension of 25 dyne-cm.

The ink was used in the ink jet printing of bare tinplate and aluminum cans as well as acrylic coated aluminum and tinplate cans. The printed indicia dried very quickly to form blue images displaying excellent adhesion to the substrate. Subjecting the cans to sterilization in the presence of steam at 250° F. for 40 minutes or 260° F. for 8.7 minutes, resulted in a visible color change of the printed indicia from blue to red. During more than 1,000 hours of operation of the jet printing units with the ink composition, evaporative losses from the ink supply were compensated for by the addition, as needed, of a makeup composition containing volatile solvents.

When the above example is repeated substituting Janus Green B or Janus Black for the Indoine Blue dye employed therein, comparable results are obtained.

EXAMPLE 2

Example 1 was repeated except the cans were subjected to hot water at about 120° F. to 212° F. for a period of time ranging up to 60 minutes. No change or transition in color was observed. This example illustrates that the compositions of the invention are thermotropic at an elevated temperature of at least about 215° F., i.e. they function as high-temperature sterilization indicators and do not undergo a color change in the absence of these conditions.

EXAMPLE 3

The following composition was used to mark plastic pouches:
39.1% Ethyl cellosolve
40.4% Methyl Alcohol
12.2% BLS-2700 phenol-formaldehyde resin
0.6% Dimethyl amine hydrochloride
1.5% FC-430 surfactant
0.9% Indoine Blue
5.1% Dimethyl sulfoxide The resulting ink had a viscosity of 1.8 cps., a resistivity of 570 ohm/cm. and a surface tension of 25 dyne-cm. Indicia were printed, using an ink jet printing technique, on polyethylene, polypropylene, nylon, vinyl chloride-vinylidene chloride copolymer (Saran), polyester and polyvinyl chloride plastic surfaces.

It will be seen from the above that the compositions of the invention are valuable sterilization indicators which can provide multiple functions in the packaging industry. For example, use of the compositions to imprint indicia on metal cans permits the packer to determine upon visual inspection of any given batch of cans that the containers have been exposed to moist temperatures above about 215° F. Additionally, the presence of such visible indicia permits the ready rejection of individual containers that have not been processed and traceability of the origin of the container in the event of defects either in the container or its contents. Additionally, provision of a thermotropic ink usable in jet printing provides for obtaining the above mentioned character changes and eliminates damage to the containers caused by many of prior contact printing methods.

Finally, because the ink composition is applicable to both coated and uncoated metal and plastic substrates, they are unusually versatile affording a wide spectrum of suitable substrates on which they may be used.

We claim:

1. A thermotropic ink composition suitable for use in contact or ink jet printing operations comprising a solution of (a) a soluble resole resin; (b) a thermotropic dye capable of undergoing a visible change in color and (c) a solvent for said resin and dye consisting essentially of a lower aliphatic monohydric alcohol or mixture thereof, said composition undergoing a color change upon exposure to steam at a temperature of at least about 215° F.

2. An ink composition as claimed in claim 1 wherein said resole resin has a molecular weight within the range of about 1300 to about 10,000.

3. An ink composition as claimed in 2 wherein said resole resin is an alkaline catalyzed phenol-formaldehyde or resorcinol-formaldehyde condensation product in which the ratio of formaldehyde is greater than 1.

4. An ink composition as claimed in claim 2 wherein said solvent comprises a lower aliphatic monohydric alcohol or mixture thereof with one or more solvents selected from the group consisting of methyl cellosolve, ethyl cellosolve, dimethyl formamide and dimethyl sulfoxide.

5. A thermotropic ink composition suitable for use in contact or ink jet printing operations comprising a solution of (a) from about 3 to 30% by weight of a soluble resole resin having a molecular weight of about 1300 to 10,000; (b) from about 0.1 to 5% by weight of a thermotropic phenazine dye capable of undergoing a visible change in color and (c) a solvent for said dye and resin consisting essentially of a lower aliphatic monohydric alcohol, said ink composition undergoing a color change upon exposure to steam at a temperature of at least about 215° F.

6. An ink composition as claimed in claim 5 wherein said resole resin is a phenol-formaldehyde, said thermotropic dye is Indoine Blue and said solvent is methanol.

7. An ink composition as claimed in claim 5 additionally comprising a surfactant.

8. An ink composition as claimed in claim 7 wherein said surfactant is a fluorinated alkyl ester.

9. A thermotropic ink composition suitable for use in contact or ink jet printing on coated and uncoated metal and plastic surfaces comprising a solution of: about 5% phenol formaldehyde resole resin derived from the alkaline catalyzed condensation of phenol and formaldehyde in which the ratio of formaldehyde to phenol is greater than 1, said resole resin having a molecular weight of about 1300 to 10,00; about 1% of an azo-phenazine thermotropic dye, about 47% methanol, about 47% methyl cellosolve, and about 0.01% fluorinated alkyl ester surfactant, said composition undergoing a color change upon exposure to steam at a temperature of at least about 215° F.

10. A thermotropic ink composition suitable for use in contact or ink jet printing on coated and uncoated metal and plastic surfaces comprising a solution of: about 12.2% phenol formaldehyde resole resin derived from the alkaline catalyzed condensation of phenol and formaldehyde in which the ratio of formaldehyde to phenol is greater than 1, said resole resin having a molecular weight of about 1300 to 10,000; about 39.1% ethyl cellosolve, about 40.4% methanol, about 0.6% dimethylamine hydrochloride, about 1.5% of a fluorinated alkyl ester surfactant, about 5.1% dimethyl sulfoxide and about 0.9% of an azo-phenazine thermotropic dye, said composition undergoing a color change upon exposure to steam at a temperature of at least about 215° F.

11. An ink composition as claimed in either of claims 9 or 10 in which the azo-phenazine dye is an Indoine Blue dye.

12. A method of indicating steam sterilization of articles which comprises applying markings to a surface of said articles using a thermotropic ink composition comprising a solution of (a) a soluble resole resin (b) a thermotropic dye and (c) a solvent for said resin and dye and exposing the marked articles to steam at a temperature of at least about 215° F. for a time sufficient to effect a visible color change in said markings.

13. A method as claimed in claim 12 wherein said articles are coated or uncoated tinplate and aluminum cans.

14. A method as claimed in claim 13 in which said resole resin is a phenol-formaldehyde resin having a molecular weight of about 1300 to 10,000.

15. A method as claimed in claims 12, 13, or 14 wherein said dye is a phenazine dye.

16. A method as claimed in claims 12, 13, 14, or 15 wherein said solvent consists essentially of a lower aliphatic monohydric alcohol.

17. A method as claimed in claim 16, wherein said markings are applied by jet ink printing of said thermotropic ink composition.

18. A method as claimed in claim 16 wherein said markings are applied by contact printing of said thermotropic ink composition.

19. A method of indicating steam sterilization of coated or uncoated tinplate or aluminum or plastic containers which comprises:
applying markings to a surface of said container using a thermotropic ink composition comprising a solution of (a) from about 3 to 30% by weight a soluble phenol-formaldehyde resole resin: (b) from about 0.1 to 5% by weight of a thermotropic phenazine dye (c) from about 0.01 to 0.1% by weight of a fluorinated alkyl ester surfactant and (d) sufficient amount of a solvent for said resin and dye to constitute a 100% solution said solvent consisting essentially of a lower aliphatic monohydric alcohol or mixture thereof;
and exposing the marked containers to steam at a temperature of at least about 215° F. for a time sufficient to effect a visible color change in said markings.

20. A method as claimed in claim 19 wherein said dye is Indoine Blue.

21. A method as claimed in claim 19 wherein said markings are applied by jet ink printing of said thermotropic ink composition.

22. A method as claimed in 19 wherein said markings are applied by contact printing of said thermotropic ink composition.

23. A method as claimed in claim 19 wherein said plastic containers are comprised of polyethylene, polypropylene, vinyl chloride-vinylidene chloride copolymer, polyester, polyvinyl or polyamide synthetic resins.

24. A method of indicating steam sterilization of coated or uncoated tinplate or aluminum containers which comprises:
applying markings to a surface of said container using a thermotropic ink composition comprising: about 5% phenol formaldehyde resole resin derived from the alkaline catalyzed condensation of phenol and formaldehyde in which the ratio of formaldehyde to phenol is greater than 1, said resole resin having a molecular weight of about 1300 to 10,000; about 1% of an azo-phenazine thermotropic dye, about 47% methanol, about 47% methyl cellosolve, and about 0.01% fluorinated alkyl ester surfactant, said composition undergoing a color change upon exposure to steam at a temperature of at least about 215° F.

25. A method for indicating steam sterilization of coated and uncoated metal and plastic surfaces which comprises:
applying markings to said surfaces using a thermotropic ink solution comprising: a solution of about 12.2% phenol formaldehyde resole resin derived from the alkaline catalyzed condensation of phenol and formaldehyde in which the ratio of formaldehyde to phenol is greater than 1, said resole resin having a molecular weight of about 1300 to 10,000; about 39.1% ethyl cellosolve, about 40.4% methanol, about 0.6% dimethylamine hydrochloride, about 1.5% of a fluorinated alkyl ester surfactant, about 5.1% dimethyl sulfoxide and about 0.9% of an azo-phenazine thermotropic dye, said composition undergoing a color change upon exposure to steam at a temperature of at least about 215° F.

26. A method as claimed in either of claims 24 or 25 wherein the azo-phenazine dye is an Indoine Blue dye.

* * * * *